United States Patent [19]

Ellis, Jr. et al.

[11] Patent Number: 5,354,857
[45] Date of Patent: Oct. 11, 1994

[54] METAL PHTHALOCYANINE CATALYSTS

[75] Inventors: Paul E. Ellis, Jr., Downingtown; James E. Lyons, Wallingford, both of Pa.

[73] Assignee: Sun Company, Inc. (R&M), Philadelphia, Pa.

[21] Appl. No.: 99,281

[22] Filed: Jul. 29, 1993

Related U.S. Application Data

[62] Division of Ser. No. 862,038, Apr. 2, 1992, Pat. No. 5,254,740.

[51] Int. Cl.$^5$ .................................. C07D 487/22
[52] U.S. Cl. ................................ 540/135; 540/140
[58] Field of Search ............................. 540/135, 140

[56] References Cited

U.S. PATENT DOCUMENTS 4,537,713 8/1985 Eckert ................................ 540/135
4,895,682 1/1990 Ellis et al. ...................... 260/410.9 R
5,093,491 3/1992 Ellis et al. ........................... 540/135

OTHER PUBLICATIONS

W. Kalz et al., "Darstellung and Charakterisierung von Biscyanophthalocyaninatoferraten (III)" (Preparation and Characterisation of Biscyanophythalocyaninatoferrates (III), Z. Naturforsch, B. Anorg. Chem. Org. Chem., 39b (1983) pp. 1478–1489.

*Primary Examiner*—James H. Reamer
*Attorney, Agent, or Firm*—Q. Todd Dickinson; Stephen T. Falk

[57] ABSTRACT

As a new composition of matter, alkali metal or ammonium or tetraalkylammonium diazidoperfluorophthalocyanatoferrate. Other embodiments of the invention comprise compositions wherein the metal of the coordination complex is cobalt, manganese and chromium.

9 Claims, No Drawings

METAL PHTHALOCYANINE CATALYSTS

The Government of the United States of America has rights in this invention pursuant to Cooperative Agreement No. DE-FC21-90MC26029 awarded by the U.S. Department of Energy.

This is a divisional of copending application Ser. No. 07/862,038 filed on Apr. 2, 1992, now U.S. Pat. No. 5,254,740.

BACKGROUND OF THE INVENTION

Azide-activated metal phthalocyanine ligands have been disclosed in U.S. Pat. Nos. 4,895,682 and 5,093,491 to Ellis, Lyons and Myers, as catalysts for the oxidation of alkanes with air or oxygen. These patents disclose macrocycles which contain an azide group attached to the phthalocyanine ring.

DESCRIPTION OF THE INVENTION

The present invention involves in one embodiment the preparation and use as alkane oxidation catalysts of metal phthalocyanine compounds having specifically two azide groups. A general formula for such catalysts is:

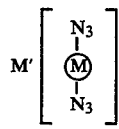

where M is iron, cobalt, manganese or chromium, $N_3$ is azide, (M) is phthalocyanine and M' is alkali metal, such as sodium, potassium or lithium, or ammonium or tetraalkylammonium such as tetrabutylammonium.

The preparation of the metal phthalocyanine diazide according to this embodiment of the invention may be accomplished by reaction of metal phthalocyanine halide with an alkali metal or ammonium or tetraalkylammonium azide. The reaction may be conducted at ambient conditions, preferably with a large weight excess of the azide.

In one embodiment of the invention, the preparation of a metal phthalocyanine azide occurs in situ in an alkane oxidation process. In this embodiment, an alkane is contacted with oxygen-containing gas and a catalyst comprising metal phthalocyanine and alkali metal or ammonium or tetraalkylammonium azide.

Preferably, the catalyst used according to the invention is a metal perhalogenated phthalocyanine, as disclosed in application Ser. No. 568,116 filed Aug. 16, 1990 by P. E. Ellis, Jr. et al, the disclosure of which is incorporated herein by reference "Perhalogenated", as used herein, refers to a degree of ligand halogenation which is preferably at least 70%, more preferably at least 90%. The term, "phthalocyanine" as used herein, includes such halogenated ligands.

A preferred compound for use according to this embodiment of the invention is sodium diazidoperfluorophthalocyanatoferrate, $Na[Fe(FPc)(N_3)_2]$ where F indicates substitution of at least 90% of the hydrogen atoms in the ligand with fluorine, Pc is phthalocyanine ligand and $N_3$ is azide.

In another embodiment of the invention, oxidation of alkanes is carried out in the presence of a metal phthalocyanine or halide thereof, for example iron perfluorophthalocyanine, and an alkali metal or ammonium or tetraalkylammonium azide, under conditions as used previously in the oxidation of alkanes with metal phthalocyanine azides. Although the invention is not to be limited by any theory, it is believed that in this embodiment, the metal phthalocyanine and the azide react to form metal phthalocyanine azide in situ, which then catalyzes the oxidation reaction.

In this embodiment of the invention, the metal phthalocyanine and the alkali metal or ammonium or tetraalkylammonium azide may be added separately or together to the reaction mixture containing the alkane to be oxidized. The reaction conditions used are generally those disclosed in column 3 of U.S. Pat. No. 4,895,682 supra, for oxidation using azide-activated metal phthalocyanines, the disclosure of which is hereby incorporated by reference.

EXAMPLES

The invention will be further described with reference to the following examples:

Example 1

Iron phthalocyanine chloride, Fe(FPc)Cl, was prepared by refluxing the known complex, FeFPc, in chlorobenzene. The product, Fe(FPc)Cl was reacted metathetically with a tenfold weight excess of sodium azide in methanol at room temperature for 48 hours. The reaction product was evaporated to dryness, washed with water and dried.

The major product, a dark green solid, was a material having two azide bands in the infrared ($\nu$N-N 1999 $cm^{-1}$ and 2030 $cm^{-1}$), believed to be the anionic diazido complex, $Na[Fe(FPc)(N_3)_2]$. Iron perfluorophthalocyanine monoazide, $Fe(FPcN_3)$, was apparently produced as a minor product.

Example 2

The diazido complex prepared in Example 1 was used for light alkane oxidation by stirring 0.0125 millimole of the complex in 25 ml of benzene containing 7 grams of isobutane under 100 psig of oxygen at the temperature designated in Table 1 below for the time indicated. Tert-butyl alcohol and acetone were the major products. The results are shown in Table I.

Comparison Example

For comparison, Runs 4 to 8 shown in Table II were carried out under the indicated conditions for the oxidation of isobutane with air using as catalyst iron-phthalocyanine complex in Run 4, iron-phthalocyanine nitride in Run 5, iron-perfluorophthalocyanine in Run 6 and iron-perfluorophthalocyanine monoazide in Runs 7 and 8. Comparison of Runs 2 and 3 of Table I with Runs 7 and 8 of Table II show that the diazide complex of Table I gave results similar to the monoazide complex of Table II. In addition, diazide complexes have been found to have superior shelf stability to monoazide complexes.

TABLE I

Reactions of Isobutane with Oxygen Catalyzed by $Na[FeFPc(N_3)_2]$

| Run | Catalyst mmoles | T °C. | t, hours | T.O.[a] | Selectivity to t-butyl alcohol |
|---|---|---|---|---|---|
| 1 | 0.021 | 80 | 6 | 743 | 81 |
| 2 | 0.0125 | 80 | 6 | 1029 | 82 |

TABLE I-continued

TABLE III

Oxidation of Propane[a] Catalyzed by Iron Perfluorophthalocyanine Complexes

| | Complex | mmoles | Solvent, | T, °C. | t, Hrs. | TON[b] | IPA/ Acetone[c] |
|---|---|---|---|---|---|---|---|
| 9 | Fe(FPc) | 0.023 | Benzene | 125 | 3 | 0 | — |
| 10 | Fe(FPc)N$_3$ | 0.028 | Benzene | 125 | 6 | 48 | 0.7 |
| 11 | Fe(FPc) | 0.023 | CH$_3$CN | 125 | 3 | 57 | 0.7 |
| 12 | Fe(FPc) + NaN$_3$ | 0.028 | CH$_3$CN | 125 | 3 | 98 | 0.7 |
| 13 | Fe(FPc) | 0.028 | CH$_3$CN | 150 | 3 | 460 | 0.3 |
| 14 | Fe(FPc) + NaN$_3$ | 0.028 | CH$_3$CN | 150 | 3 | 567 | 0.4 |
| 15 | Fe(FPc)N$_3$ | 0.028 | CH$_3$CN | 150 | 3 | 754 | 0.7 |
| 16 | Fe(FPc)Cl | 0.028 | CH$_3$CN | 150 | 3 | 606 | 0.7 |
| 17 | Fe(FPc)N$_3$ | 0.028 | C$_6$H$_5$CN | 150 | 3 | 1210 | 0.6 |

[a]Propane (1.36 mol) was added to the solvent (48 ml) containing the catalyst. The reaction mixture was stirred at the designated temperature under 1000 psig of air in a glass-lined autoclave. Liquids and gases were analyzed by gas chromatography. Production of carbon oxides never exceeded 10% of total products. Isopropyl alcohol and acetone exceeded 85 mole % of carbon-containing reaction products in all cases.
[b]Moles of acetone plus isopropyl alcohol formed per mole of catalyst used.
[c]Molar ratio of isopropyl alcohol to acetone formed.

Reactions of Isobutane with Oxygen Catalyzed by Na[FeFPc(N$_3$)$_2$]

| Run | Catalyst mmoles | T °C. | t, hours | T.O.[a] | Selectivity to t-butyl alcohol |
|---|---|---|---|---|---|
| 3 | 0.0125 | 60 | 6 | 162 | 92 |

[a]Turnovers: moles of oxidate produced/mole catalyst used

TABLE II

Oxidation of Isobutane[a] Catalyzed by Metal Phthalocyanine Compounds

| Run | Catalyst | mmoles | T, °C. | t, Hrs. | TON[b] | SEL[c] |
|---|---|---|---|---|---|---|
| 4 | Fe(Pc) | 0.030 | 80 | 6 | 0 | — |
| 5 | [Fe(Pc)]$_2$N | 0.016 | 80 | 6 | 0 | — |
| 6 | Fe(FPc) | 0.023 | 80 | 6 | 0 | — |
| 7 | Fe(FPc)N$_3$ | 0.013 | 80 | 6 | 990 | 82 |
| 8 | Fe(FPc)N$_3$ | 0.013 | 60 | 6 | 156 | 92 |

[a]The catalyst was stirred in 25 ml benzene containing 6 grams isobutane under 100 psig of O$_2$ at the designated temperature for the time indicated.
[b]Turnovers: Moles O$_2$ consumed/mole catalyst used.
[c](Moles t-butyl alcohol produced/total moles liquid product) × 100.

Example 3

Propane was oxidized with air under the conditions, and with the catalysts shown in Table III. The results are shown in Table III. Runs 12 and 14 used as catalyst, iron perfluorophthalocyanine and sodium azide. Comparison of these runs with Runs 10, 15 and 17, in which the catalyst was metal phthalocyanine azide, indicates that the catalyst of Runs 12 and 14 was active for the reaction, though apparently less active at 150° C. than the catalyst of Runs 10, 15 and 17 (567 turnovers in Run 14 against 754 turnovers in Run 15 ).

The invention claimed is:

1. A composition of matter having the following formula $$M'\left[\begin{array}{c} N_3 \\ | \\ \text{\textcircled{M}} -X \\ | \\ N_3 \end{array}\right]$$

wherein M is Fe, Co, Mn or Cr; N$_3$ is azide; 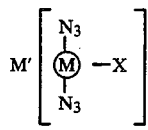 is phthalocyanine; X is halogen substituted for hydrogen atoms in the phthalocyanine molecule; and M' is alkali metal or ammonium or tetraalkylammonium.

2. The composition of claim 1 wherein M is iron.

3. The composition of claim 1 wherein said phthalocyanine is perhalogenated.

4. The composition of claim 3 wherein said halogen is fluorine, chlorine or bromine.

5. The composition of claim 4 wherein said halogen is fluorine.

6. A composition of matter comprising alkali metal, ammonium or tetraalkylammonium diazidohalophthalocyanine metal complex, wherein said metal comprises iron, cobalt, manganese or chromium.

7. The composition of claim 6 wherein said complex is perhalogenated.

8. The composition of claim 7 wherein said complex is perfluorinated.

9. As a new composition of matter, alkali metal or ammonium or tetraalkylammonium diazidoperfluorophthalocyanatoferrate.

* * * * *